United States Patent
Le Bon et al.

(10) Patent No.: US 7,842,094 B2
(45) Date of Patent: Nov. 30, 2010

(54) CEMENT SPACER FOR ACETABULAR CUP

(75) Inventors: Franck Le Bon, Evrecy (FR); Alain Richard, Epron (FR); Jean-Pierre Brée, F (FR); Philippe Lavieille, Caen (FR)

(73) Assignee: Benoist Girard SAS (FR)

( * ) Notice: Subject to any disclaimer, the term of this patent is extended or adjusted under 35 U.S.C. 154(b) by 205 days.

(21) Appl. No.: 12/156,790

(22) Filed: Jun. 4, 2008

(65) Prior Publication Data
US 2009/0082876 A1    Mar. 26, 2009

(30) Foreign Application Priority Data
Sep. 26, 2007  (GB) .............................. 0718821.2

(51) Int. Cl.
*A61F 2/30* (2006.01)
*A61F 2/34* (2006.01)

(52) U.S. Cl. ............... 623/22.38; 623/22.21; 623/22.37

(58) Field of Classification Search ... 623/19.11–19.13, 623/22.21–22.39, 23.43, 23.48
See application file for complete search history.

(56) References Cited

U.S. PATENT DOCUMENTS

| | | | |
|---|---|---|---|
| 4,285,071 A | 8/1981 | Nelson et al. | |
| 4,417,571 A | 11/1983 | Nelson et al. | |
| 4,563,778 A | 1/1986 | Roche et al. | |
| 4,566,138 A | 1/1986 | Lewis et al. | |
| 4,666,450 A | * | 5/1987 | Kenna ...................... 623/22.28 |
| 4,955,325 A | 9/1990 | Zarnowski et al. | |
| 5,116,380 A | 5/1992 | Hewka et al. | |
| 5,314,489 A | 5/1994 | Hoffman et al. | |
| 5,916,268 A | 6/1999 | Schollner et al. | |
| 6,123,730 A | 9/2000 | Ling et al. | |
| 2004/0019380 A1 | 1/2004 | Baege et al. | |

FOREIGN PATENT DOCUMENTS

DE    9300471 U1    3/1993

OTHER PUBLICATIONS

European Search Report, EP 08253068, dated Dec. 15, 2008.

* cited by examiner

*Primary Examiner*—David H Willse
*Assistant Examiner*—Megan Wolf
(74) *Attorney, Agent, or Firm*—Lerner, David, Littenberg, Krumholz & Mentlik, LLP

(57) ABSTRACT

An acetabular cup has a shell having a recess therein, the recess is open to an outer surface of the shell. The recess has an enlarged portion spaced from the shell outer surface with a diameter greater than the diameter of the opening at the surface. An insert is provided for insertion into the recess in the shell outer surface. The insert has a height greater than a depth of the recess and has a solid portion and a bifurcated portion having at least two side openings forming two to four sectors. A base of the sectors formed by bifurcated portion has an outwardly extending flange for insertion into the enlarged portion of the recess.

21 Claims, 2 Drawing Sheets

CEMENT SPACER FOR ACETABULAR CUP

BACKGROUND OF THE INVENTION

This invention relates to a cement spacer which can be used in a prosthetic cup and to a method of sterilization thereof.

Prosthetic cups adapted to be held in place in a receptive opening in a bone can have an outer surface provided with one or more projecting cement spacers to space the outer surface of the cup away from the receptive opening in which it is placed. The resulting gap around the cup provided by the spacer or spacers enables the thickness of cement to be controlled. Spacers of this type are well known for this purpose such as shown in U.S. Pat. Nos. 4,563,778 and 4,955,325.

The spacers can be provided in many ways but are often formed as projections on the outer surface of, for example, a prosthetic hip cup.

Products for use in surgery require sterilization and cups made from, for example, polyethylene can be sterilized with a gas plasma sterilization process. With this process the gas has to be present on all the surfaces of the product to sterilize it. There can be problems with sterilizing polyethylene cups at a level of the cement spacers. If the spacers are, for example, separate items pressed into openings in the outer surface of the cup the gas cannot penetrate behind the spacers and on the sides of any location portions which locate the spacers in the openings. Spacers of this type can, for example, be pressed into drilled holes of a diameter slightly less than location portions so that the results is an interference fit and the spacers are held rigidly in position. As mentioned above, however, this causes problems with sterilization when using a gas plasma sterilization process.

SUMMARY OF THE INVENTION

The present invention is intended to provide a construction of cement spacer which can be located in a cup but still provide the facility for sterilization.

According to the present invention a prosthetic cup adapted to be held in place in a receptive opening in a bone by cement, and having an outer surface provided with one or more projecting spacers to space said outer surface away from the surface of said receptive opening in which said spacer or spacers is or are loosely carried on said cup with a surrounding clearance gap to allow loose relative movement in all directions.

With this arrangement, because there is a gap around the spacer it is possible for the sterilizing gas or any other light media for sterilizing to penetrate behind and on the sides of the spacer.

When the cup is used in the receptive opening in the bone the gap between the sides of the spacer and the cup and the spacer between the cup and the receptive opening will be filled with cement which will lock the assembly in position.

In a preferred arrangement each of the spacers comprises a head which projects from said outer surface and a location portion which is carried in a recess in said cup with a surrounding clearance gap. The clearance gap can be between 0.01 mm and 1 mm. The recess can be undercut and the location portion can have a retentive flange which locates in the undercut to hold the spacer in position once it had been inserted.

The retention flange can have a diameter slightly greater than the inner edge of the undercut so that the flange can be pressed into position as a snap-fit and will then prevent the spacer from being removed outwardly by the flange locating beneath the undercut. The inner end of the location portion preferably has one or more abutment feet to space it away from the inner end wall of the recess.

The outer end of the head can have an opening which extends inwardly into the recess. Thus, with this construction, the opening can extend into a chamber extending through the inner end of the location portion. This chamber preferably has a side opening or openings which extend through the side wall of the location portion and, of required, can be arranged to extend into a part of the side wall of the head.

In a preferred construction the outer end of the spacer, or each of the spacers, is dome-shaped and the insertion portion can be substantially cylindrical. The spacers can be made from any suitable material, for example a synthetic plastics material or a metal.

The invention also includes a method of sterilizing a prosthetic cup of the kind set forth above which includes applying a gas plasma with a pressure which is sufficient to enter the gap surrounding the spacer to allow the gas to sterilize the walls of the gap and the spacer.

Various aspects of the invention are accomplished by an acetabular cup which has a shell having a recess therein. The recess is open to an outer surface of the shell and has an enlarged portion spaced from the outer surface having a diameter greater than the diameter of the opening at the outer surface. An insert is provided for insertion into the recess in the outer shell. The insert has a height greater than a depth of the recess and has a solid portion and a bifurcated portion having at least two side openings thereby forming two to four sectors. A base of each sector of the bifurcated portion having an outwardly extending flange for insertion into the enlarged portion of the recess. The base of the bifurcated portion may include a plurality of outwardly extending feet for engaging a bottom surface of the recess. The bifurcated portion can have four side openings forming four deflectable arms. Each arm preferably includes a foot for engaging the bottom surface of the recess and spacing the insert therefrom. The flange preferably has an inwardly chamfered outer surface to facilitate insertion into the recess. The solid insert portion may have a bore therein extending from the outer surface of the insert to an intersection of the side openings in the bifurcated insert opening. Preferably the outer cup surface includes at least three inserts located in corresponding recesses in the cup.

BRIEF DESCRIPTION OF THE DRAWINGS

The invention can be performed in various ways but one embodiment will now be described by way of example and with reference to the accompanying drawings in which.

DETAILED DESCRIPTION

Figure 1:
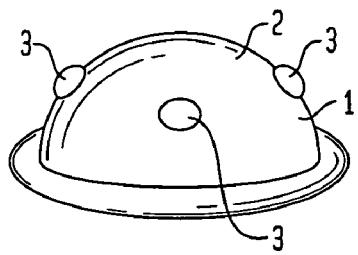
FIG. 1 is an isometric view of a prosthetic hip cup made from polyethylene or metal and incorporating cement spacers according to the present invention.
Figure 2:
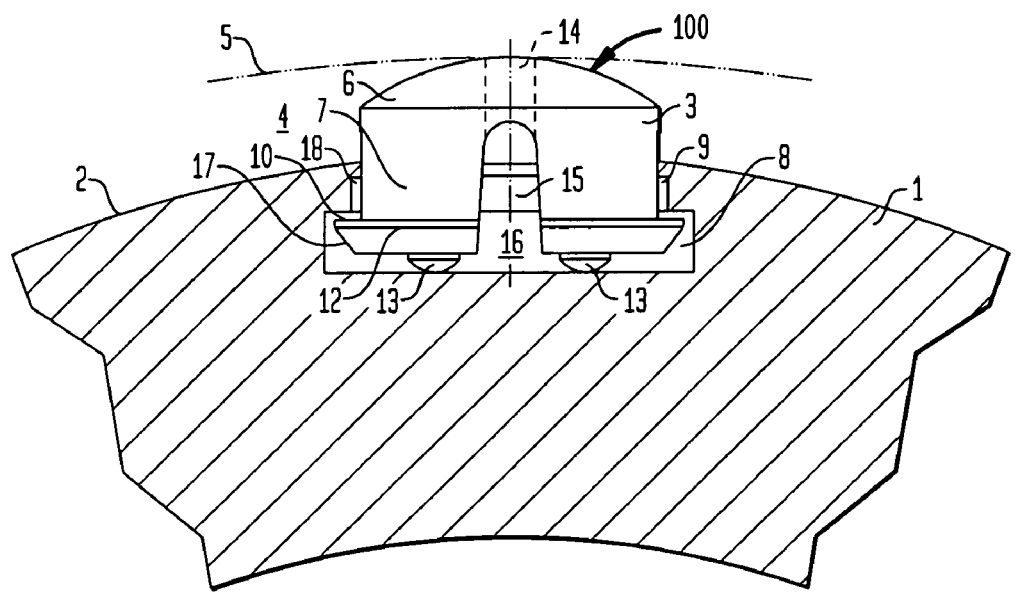
FIG. 2 is a side view of a cement spacer according to the invention in position in the outer surface of the cup shown in FIG. 1.
Figure 3:
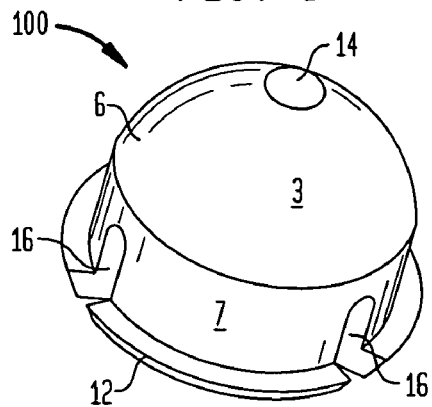
FIG. 3 is an isometric view from above of the spacer shown in FIG. 2.
Figure 4:
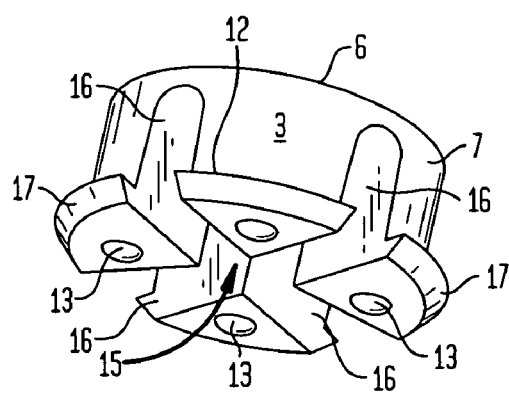
FIG. 4 is an isometric view from below of the spacer shown in FIGS. 2 and 3.

As shown in FIGS. 1 to 4 of the drawings the prosthetic insert generally denoted as 100 which is adapted to be placed on a prosthetic cup held in place in a receptive opening in a bone by bone cement. The cup according to the present invention, is in the form of an acetabular cup 1 which is preferably formed from polyethylene. The outer surface 2 of the cup 1 is provided with four projecting spacers 100. Spacers 100 have a body 3 which can act to space the outer surface 2 of the cup away from the surface of a receptive opening 4 the surface of which is indicated by chain line 5 in FIG. 2.

Each of the spacer bodies 3 comprises a head 6 which projects from the outer surface 2 and a location portion 7 which is carried in a recess 8 with a surrounding clearance gap 9.

The recess 8 is undercut at 10 and the location portion 7 has a retention flange 12 which locates within the undercut 10. The dimensions of the flange and the undercut are arranged so that the spacer is a snap-fit but is loose so that, after insertion, there is relative movement in all directions. The width of the gap 9 around the location portion 7, including the flange 12, is preferably between 1 mm and 0.01 mm.

The lower surface of the location portion 7 carries four abutment feet or spacers 13 which project downwardly below the flange 12 and which, when the spacer is initially inserted, rest on the bottom of the recess 8. Due to the gap however, and as mentioned above, the spacer is loosely carried and can be moved in all directions including having feet 13 extending away from the lower surface of the recess 8.

The outer end of the head 6 has an opening 14 which extends inwardly into the recess 8 via a chamber 15 which extends through the inner end of the location portion 7. The chamber 15 has four side openings 16 (best shown in FIG. 4) which extend through the side wall of the location portion 7 and into a part of the side wall of the head 6.

The outer end of the head 6 of body 3 is substantially dome-shaped and the insert portion 7 is substantially cylindrical.

The lower end of the flange 12 is chamfered as indicated by reference numeral 17 and the outer end of the recess 8 in cup 100, which is circular to take the flange 12, is also chamfered or countersunk at 18. This chamfering assists the snap-fit.

Figure 5:
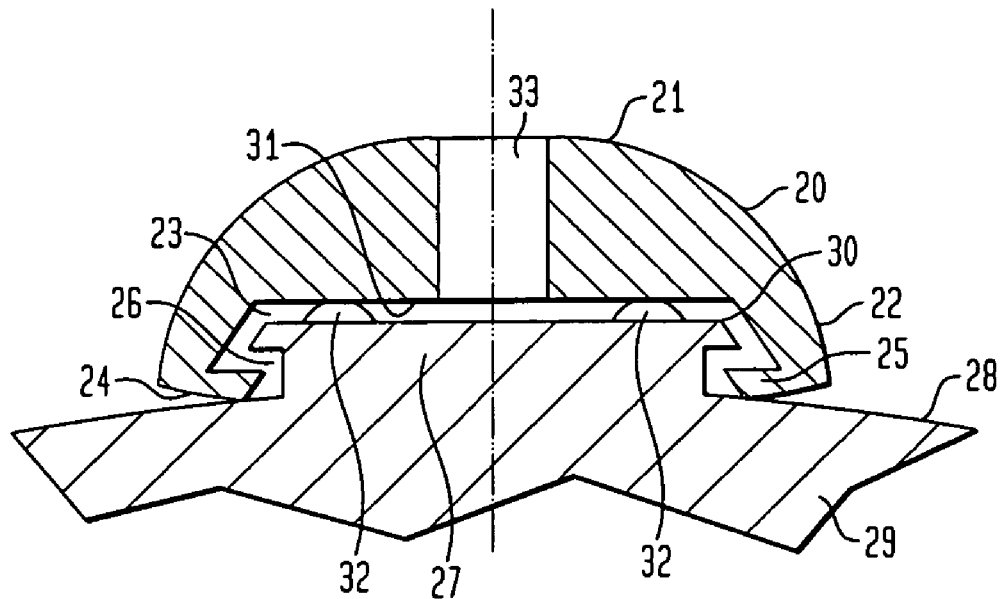
FIG. 5 is a cross-section diagrammatic view of an alternative construction of a spacer.

FIG. 5 shows an alternative construction in which spacer 20 comprises a head portion 21 and an engagement portion 22 which has a recess 23 the outer edge 24 of which has an inwardly projecting flange 25 which is dimensioned to loosely engage beneath an undercut 26 on a co-operating abutment 27 provided on the outer surface 28 of an insert 29. A clearance gap 30 is provided between the abutment 27 and the inner surface 31 of the recess 23 and the spacer therefore engages loosely on the abutment 27 with a snap fit. The clearance gap can be between 1 mm and 0.01 mm.

The abutment 27 is provided with four abutment feet 32 to space it away from the inner surface 31 of the recess 23. The outer end of the head 21 of the spacer has an opening 33 which extends into the recess 23. This construction can be used in a similar manner described in the construction shown in FIGS. 1, 2 and 3.

Figure 6:
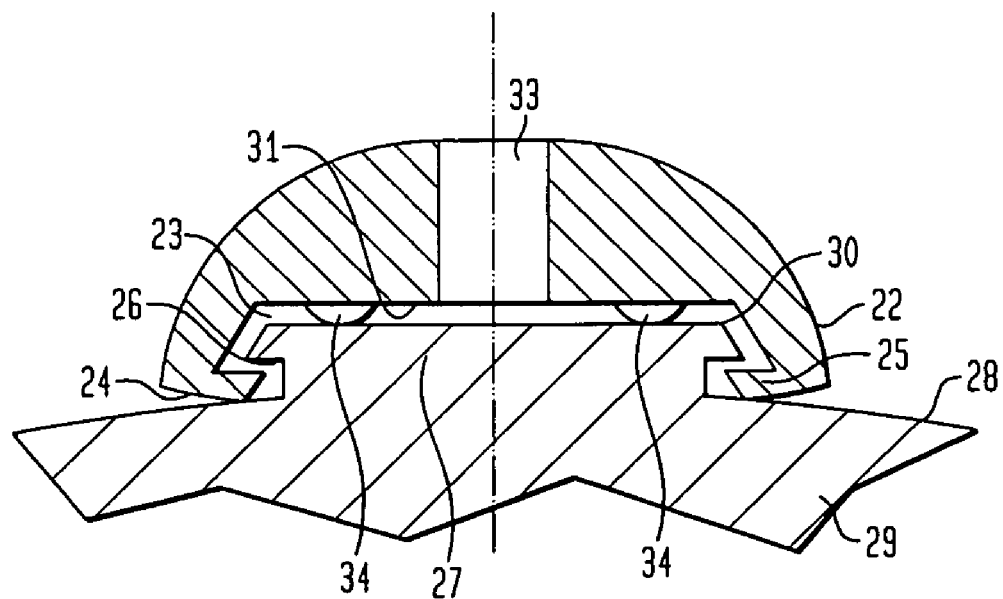
FIG. 6 is a cross-section diagrammatic view of another alternative construction.

FIG. 6 shows an alternative construction similar to that shown in FIG. 5 and the same reference numerals are used to indicate similar parts. In this construction the abutment feet 32 are replaced by feet or spacers 34 which are provided on the inner surface 31 of the recess 23 to provide a gap 30.

The invention also includes a method of sterilizing a prosthetic cup of the type described above and which includes applying a gas plasma in a suitable environment with a pressure which is sufficient to enter the gap 8 between the spacer 3 and insert 1 or into the gap 30 between the abutment 27 and the spacer 20 to allow the gas plasma to sterilize the walls of the gap and the spacer, at the same time as sterilizing the insert.

The various parts can be made of any convenient material, for example a synthetic plastics material, a metal or a bone cement (PMMA) and in the embodiments described the cup 15 is made of a polyethylene material.

The invention therefore provides an arrangement whereby the retentive shape of spacer can be used to ensure a good fixation and the various features help the gas to penetrate behind and on the sides of the spacer.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular cup for cemented implantation in an acetabulum comprising:
   a shell having a recess with a bottom surface therein forming an opening open to an outer surface of the shell and having an enlarged portion spaced from the outer surface having a diameter greater than the diameter of the opening and including the bottom surface; and
   an insert for insertion into the recess in the outer shell to be held loosely therein, the insert having a height greater than a depth of the recess and having a solid portion and a bifurcated portion having at least two side openings, a base of the bifurcated portion having an outwardly extending flange for insertion into the enlarged portion of the recess the base of the bifurcated portion including a plurality of spacers contacting the bottom surface to form a gap between the base of the bifurcated portion and the recess bottom surface for ingress of bone cement.

2. The acetabular cup as set forth in claim 1 wherein the spacers at the base of the bifurcated portion are in the form of outwardly extending protrusions for engaging the bottom surface of the recess.

3. The acetabular cup as set forth in claim 2 wherein the bifurcated portion includes four side openings forming four deflectable arms, each arm including a protrusion for engaging the bottom surface of the recess and spacing the insert therefrom.

4. The acetabular cup as set forth in claim 3 wherein the flange has an inwardly chamfered outer surface.

5. The acetabular cup as set forth in claim 4 wherein the solid insert portion has a bore therein extending from the outer surface of the insert to an intersection of the side openings in the bifurcated insert opening.

6. The acetabular cup as set forth in claim 1 wherein the outer cup surface includes at least three inserts located in corresponding recesses in the cup.

7. An acetabular cup comprising:
   a shell having an outwardly facing surface including at least three stepped coupling recesses thereon, the coupling recesses each having a first portion with a first diameter and a second portion with a second smaller diameter forming a recessed step therebetween and a bottom surface; and
   an insert having a solid portion and a bifurcated portion and dimensioned to loosely fit in the recesses surrounded by a clearance gap, the bifurcated portion having at least two arms each having a flange for insertion into the recessed step the arms having a base with a protrusion contacting the bottom surface of the recess forming a gap therebetween for ingress of bone cement.

8. The acetabular cup as set forth in claim 7 wherein the bifurcated portion includes four side openings forming four deflectable arms, each arm including a protrusion for engaging the bottom surface of the recess and spacing the insert therefrom.

9. The acetabular cup as set forth in claim 8 wherein the flange has an inwardly chamfered outer surface.

10. The acetabular cup as set forth in claim 9 wherein the solid insert portion has a bore therein extending from an outer surface of the insert to an intersection of the side openings in the bifurcated insert portion.

11. The acetabular cup as set forth in claim 7 wherein the outer cup surface includes at least three inserts located in the corresponding at least three coupling recesses in the cup.

12. An acetabular cup adapted to be held in place in a receptive opening in an acetabulum by cement, comprising an outer surface provided with a plurality of recesses each having a projecting spacer having an outer surface located to space said outer cup surface away from a surface of said receptive opening and in which said spacers are loosely carried in the recesses in the outer surface of said cup with a surrounding clearance gap to allow loose relative movement of the spacer in the recess in all directions, the spacer having a bottom surface with a protrusion with the protrusion forming a gap between the spacer bottom surface and a bottom surface of the recess for ingress of bone cement.

13. The cup as claimed in claim 12 in which each of said spacers comprise a head and sidewalls having a bottom surface, wherein the head projects from said cup outer surface and the sidewalls are carried in the recess in said cup with the recess bottom surface spaced from the sidewall bottom surface by the protrusion.

14. The cup as claimed in claim 13 in which the surrounding clearance gap is between 0.01 mm and 1 mm.

15. The cup as claimed in claim 13 in which said recess has an undercut portion and said sidewall has a retention flange which locates in said undercut portion.

16. The cup as claimed in claim 15 in which said retention flange has a diameter slightly greater than a diameter of an inner edge of said undercut recess portion so that the flange can be pressed into position with the flange locating in the undercut portion.

17. The cup as claimed in claim 16 in which said undercut portion receives the retention flange as a snap fit.

18. The cup as claimed in claim 17 in which the head has a central opening which extends inwardly towards the recess bottom surface.

19. The cup as claimed in claim 18 in which said central opening extends into a chamber formed within the sidewalls.

20. The cup as claimed in claim 19 in which the sidewalls having openings extending into said chamber.

21. The cup as claimed in claim 12 in which said spacers each comprise a head portion and an engagement portion, the engagement portion including the spacer bottom surface has an outer edge which has projecting flange, the flange is dimensioned to loosely engage beneath an undercut in the recess and has a protrusion to provide the surrounding clearance gap between the spacer bottom surface and the recess bottom surface.

* * * * *

UNITED STATES PATENT AND TRADEMARK OFFICE
CERTIFICATE OF CORRECTION

PATENT NO. : 7,842,094 B2  Page 1 of 1
APPLICATION NO. : 12/156790
DATED : November 30, 2010
INVENTOR(S) : Franck Le Bon et al.

It is certified that error appears in the above-identified patent and that said Letters Patent is hereby corrected as shown below:

Column 6, line 11, "said undercut recess portion so that" should read --said recess so that--.
Column 6, line 26, "has projecting flange" should read --has a projecting flange--.

Signed and Sealed this
Twenty-ninth Day of November, 2011

David J. Kappos
*Director of the United States Patent and Trademark Office*